US012691245B2

(12) United States Patent
Walker

(10) Patent No.: US 12,691,245 B2
(45) Date of Patent: Jul. 28, 2026

(54) VENTILATOR

(71) Applicant: Westport Fuel Systems Canada Inc., Vancouver (CA)

(72) Inventor: James D. Walker, Malvern (GB)

(73) Assignee: Westport Fuel Systems Canada Inc., Vancouver (CA)

( * ) Notice: Subject to any disclaimer, the term of this patent is extended or adjusted under 35 U.S.C. 154(b) by 815 days.

(21) Appl. No.: 17/917,915

(22) PCT Filed: Apr. 9, 2021

(86) PCT No.: PCT/CA2021/050480
§ 371 (c)(1),
(2) Date: Oct. 7, 2022

(87) PCT Pub. No.: WO2021/203208
PCT Pub. Date: Oct. 14, 2021

(65) Prior Publication Data
US 2023/0149657 A1      May 18, 2023

Related U.S. Application Data

(60) Provisional application No. 63/008,643, filed on Apr. 10, 2020.

(51) Int. Cl.
A61M 16/12          (2006.01)
A61M 16/00          (2006.01)
(Continued)

(52) U.S. Cl.
CPC ........ A61M 16/125 (2014.02); A61M 16/024 (2017.08); A61M 16/0883 (2014.02);
(Continued)

(58) Field of Classification Search
CPC .............. A61M 16/009; A61M 16/024; A61M 16/049; A61M 16/0883; A61M 16/12;
(Continued)

(56) References Cited

U.S. PATENT DOCUMENTS 6,041,777 A * 3/2000 Faithfull ........... A61M 16/0054
128/200.24
2002/0005197 A1* 1/2002 DeVries ................ A61M 16/20
128/204.21
(Continued)

OTHER PUBLICATIONS

International Search Report and Written Opinion of the International Searching Authority, mailed Jun. 14, 2021.

*Primary Examiner* — Joseph D. Boecker
(74) *Attorney, Agent, or Firm* — Larry Kyle

(57)          ABSTRACT

There is a ventilator for mechanical ventilation during a breathing cycle including an inhalation cycle and an exhalation cycle. The ventilator is configurable to be in fluid communication with a supply of a first fluid. The ventilator includes an inhalation pathway and an exhalation pathway. A first fluid injector is in fluid communication with the supply of the first fluid for injecting the first fluid. The inhalation pathway receives the first fluid injected by the first fluid injector. A controller is operatively connected with the first fluid injector and programmed to selectively actuate the first fluid injector to inject the first fluid, which is received within the inhalation pathway such that an inhalation pressure in the inhalation pathway is within a predetermined range during the inhalation cycle.

11 Claims, 10 Drawing Sheets

(51) Int. Cl.

| | |
|---|---|
| *A61M 16/04* | (2006.01) |
| *A61M 16/08* | (2006.01) |
| *A61M 16/10* | (2006.01) |
| *A61M 16/20* | (2006.01) |

(52) U.S. Cl.
CPC .......... *A61M 16/12* (2013.01); *A61M 16/202* (2014.02); *A61M 2016/0027* (2013.01); *A61M 16/009* (2013.01); *A61M 16/049* (2014.02); *A61M 16/0866* (2014.02); *A61M 16/107* (2014.02); *A61M 16/201* (2014.02); *A61M 16/208* (2013.01); *A61M 2202/0208* (2013.01); *A61M 2205/3331* (2013.01); *A61M 2209/084* (2013.01)

(58) Field of Classification Search
CPC .............. A61M 16/122; A61M 16/125; A61M 16/202; A61M 16/203; A61M 16/204; A61M 16/205; A61M 16/208; A61M 2016/0027; A61M 2202/0208; A61M 2209/084
See application file for complete search history.

(56) References Cited

U.S. PATENT DOCUMENTS

| | | | | |
|---|---|---|---|---|
| 2002/0017299 | A1* | 2/2002 | Hickle | A61B 5/4821 128/205.25 |
| 2002/0058879 | A1* | 5/2002 | Faram | A61B 5/085 600/529 |
| 2004/0200477 | A1* | 10/2004 | Bleys | A61M 16/12 128/204.18 |
| 2013/0104885 | A1 | 5/2013 | Koebrich et al. | |
| 2014/0053837 | A1* | 2/2014 | Klein | A61M 16/0051 128/203.14 |
| 2014/0174443 | A1 | 6/2014 | Kroupa | |
| 2014/0190480 | A1* | 7/2014 | Cipolli | A61M 16/186 128/203.12 |
| 2015/0258299 | A1* | 9/2015 | Flanagan | A61M 16/122 128/202.16 |
| 2016/0279362 | A1 | 9/2016 | Devries et al. | |
| 2017/0043115 | A1* | 2/2017 | Murphy | A61P 11/00 |
| 2017/0304580 | A1* | 10/2017 | Jafri | A61M 16/209 |
| 2018/0304038 | A1* | 10/2018 | Jafri | A61M 16/201 |
| 2021/0213220 | A1* | 7/2021 | Brown | B01D 15/40 |

* cited by examiner

700

VENTILATOR

FIELD OF THE INVENTION

The present application relates to a ventilator for automated ventilation of a patient receiving healthcare.

BACKGROUND OF THE INVENTION

There is a need for more ventilators in order to treat
patients suffering from COVID-19 due to the spread of the
SARS-COV2 virus formerly known as the novel coronavi-
rus 2019. A ventilator, and more particularly a mechanical
ventilator, is a device that delivers controllable volumes of
fluid, and particularly in gaseous form, such as a mixture of
air and oxygen (O2), to a patient to replicate the inhalation
and exhalation cycle of their lungs. These ventilators can be
employed in a variety of ways. For example, certain patients
can breathe normally on their own but would benefit from
having an increased amount of oxygen in the air and the
ventilator can provide a supply of air with a selectable
content of oxygen. Alternatively, under some circumstances
patients are intubated with a tube from the ventilator that
pushes air (along with other fluids) into the lungs from the
ventilator. This process is performed when the patient cannot
maintain their airway, cannot breathe on their own without
assistance, or both. This can be the result of the patient
receiving anesthesia such that they will be unable to breathe
on their own during surgery, or the patient may be too sick
or injured to provide enough oxygen to the body without
assistance.

A healthy adult lung consumes around 500 millilitres of
air per breath cycle (the tidal volume) and have a breath rate
of typically 10 to 12 breaths per minute for a total gas
exchange of approximately 5 litres/minute. When a patient
is unwell there may be fluid in their lungs (pneumonia) that
reduces the capacity of the lungs and hence the tidal volume
that might be applied. There are considerations such as
fibrosis and other lung issues that may make the lung less
elastic and hence again reduce the tidal volume requirement.
Too much tidal volume for an unwell patient may give rise
to high levels of lung inlet pressure. A healthy lung would
respond to the induced volume with an intake pressure of
around 15 centimeters of water (cmH2O) (1.5 KPa). How-
ever, healthcare professionals need to vary the induced
volume according to the patient's needs, for example, per-
haps boosting the pressure up to 50 cmH$_2$O in order to get
better ventilation and more oxygen transfer. Instrumental
diagnostic feedback of a patients progress under ventilation
can come from a 'pulse optometry' finger probe that delivers
the blood (artery) oxygen level and hence indicates the
success or otherwise of the ventilation. Carbon dioxide
monitoring of the exhaled breath can also indicate the level
of gas exchange going on in the lung, which is another
measure of ventilation success.

Conventional ventilators employ the 'bag-in-the-bottle'
approach where a breath volume is controlled by the amount
of movement of a bellows system including a bellows. The
mixture of air and oxygen is controlled by a complex
electro-mechanical system of valves that feed the mixture
into the bellows. Movement of the bellows by a mechanical
mover is then employed to deliver a required volume of the
mixture per breath to the patient. In more detail, a desired
mixture ratio of air and oxygen is drawn into the bellows as
the mechanical mover extends the bellows to increase an
internal volume of the bellows. It is understood that in other
applications, alternatively or in addition to either the air or the oxygen, or to both the air and the oxygen, other fluids can
be included in the mixture, such as nitrous oxide (N$_2$O)
employed during operations for example. The volume
within the bellows is then pushed to the patient by the
mechanical mover contracting the bellows such that the
internal volume of the bellows decreases. Conventional
ventilators employ a volume-controlled-ventilation tech-
nique where a control system delivers predefined and set
movements of the bellows to deliver a required volume of
the mixture per breath to the patient. Ventilators have
evolved over the years to provide pressure-controlled-ven-
tilation (PCV) where the movement of a back of the bellows
is servo controlled in a closed-loop manner such that an
inhalation pressure to the patient is controlled. In this regard,
a pressure of the internal volume of the bellows controls the
movement of the bellows (extension and more particularly
contraction thereof) that in turn controls the inhalation
pressure to the patient.

Conventional ventilators of the bag-in-the-bottle type,
that employ either volume-controlled or pressure-controlled
ventilation, are complex and expensive to manufacture.
These types of ventilators cannot precisely control relatively
both the volume and pressure of the mixture delivered to the
patient for a variety of reasons. The bellows is a large, bulky
device that is difficult to precisely control the internal
volume in the extended and contracted states from part-to-
part. Typically, valves with large contact area around a valve
seat are employed to regulate fluid flow and it is difficult to
precisely control the amount of fluid that flows through the
valve as it is opening and closing.

The state of the art is lacking in techniques for improving
a delivery of controllable volumes of fluid, and particularly
a fluid mixture, to a patient to replicate the inhalation and
exhalation cycle of their lungs. The present apparatus and
methods provide a technique for improving the delivery of
controllable volumes of fluid or a fluid mixture to a patient
to replicate the inhalation and exhalation cycle of their
lungs.

SUMMARY OF THE INVENTION

An improved ventilator for mechanical ventilation during
a breathing cycle, which includes an inhalation cycle and an
exhalation cycle. The ventilator is configurable to be in fluid
communication with a supply of a first fluid. The ventilator
includes an inhalation pathway and an exhalation pathway.
A first fluid injector is in fluid communication with the
supply of the first fluid for injecting the first fluid. The
inhalation pathway receives the first fluid injected by the
first fluid injector. A controller is operatively connected with
the first fluid injector and programmed to selectively actuate
the first fluid injector to inject the first fluid, which is
received within the inhalation pathway such that an inhala-
tion pressure in the inhalation pathway is within a prede-
termined range during the inhalation cycle. In an exemplary
embodiment, the first fluid is air.

In an exemplary embodiment, preferably, the ventilator is
configurable to be in fluid communication with a supply of
a second fluid. The ventilator further includes a mixing
chamber in fluid communication with the first fluid injector
and with the inhalation pathway. The first fluid that is
injected by the first fluid injector is communicated to the
inhalation pathway through the mixing chamber. A second
fluid injector is in fluid communication with the supply of
the second fluid for injecting the second fluid. The second
fluid that is injected by the second fluid injector is commu-
nicated to the inhalation pathway through the mixing chamber. The controller is further programmed to selectively actuate the first fluid injector and the second fluid injector to inject the first fluid and the second fluid respectively to form a mixture of the first fluid and the second fluid in the mixing chamber for inhalation by a patient during the inhalation cycle. A mixture ratio between the first fluid to the second fluid can vary between 0:100 and 100:0. A mixture pressure of the mixture of the first fluid and the second fluid is within the predetermined range during the inhalation cycle. Preferably the second fluid is oxygen.

In another exemplary embodiment, preferably, the ventilator further includes a third fluid injector in fluid communication with the supply of the first fluid for injecting the first fluid. The exhalation pathway receives the first fluid that is injected by the third fluid injector. There is a restriction orifice in the exhalation pathway. The controller is further programmed to selectively actuate the third fluid injector to inject the first fluid, which is is received in the exhalation pathway such that an exhalation pressure in the exhalation pathway is within a predetermined range during at least a portion of the exhalation cycle.

An improved ventilator includes a first fluid rail for storage of a predetermined volume of a first fluid and a second fluid rail for storage of a predetermined volume of a second fluid. A first fluid injector is fluidly connected with the first fluid rail and a second fluid injector is fluidly connected to the second fluid rail. A mixing chamber is fluidly connected with the first fluid injector and the second fluid injector and with an inhalation pathway. A third fluid injector is fluidly connected with the first fluid rail and with an exhalation pathway. There is a mouthpiece for a patient is fluidly connected with the exhalation pathway and an APL valve fluidly connected with the inhalation pathway and the mouthpiece. A breathing-rate-control valve is fluidly connected with the exhalation pathway and a drain conduit. A controller is operatively connected with the first fluid injector; the second fluid injector, the third fluid injector and the breathing-rate-control valve and programmed to actuate the breathing-rate-control valve to generate a breathing cycle including an inhalation cycle and an exhalation cycle; selectively actuate the first fluid injector and the second fluid injector to inject the first fluid and the second fluid respectively to form a mixture of the first fluid and the second fluid in the mixing chamber for inhalation by a patient during the inhalation cycle, whereby a mixture ratio between the first fluid to the second fluid can vary between 0:100 and 100:0; and actuate the third fluid injector to generate back pressure in the exhalation pathway during an exhalation cycle. Preferably the first fluid is air and the second fluid is oxygen.

DETAILED DESCRIPTION OF PREFERRED EMBODIMENT(S)

Figure 1:
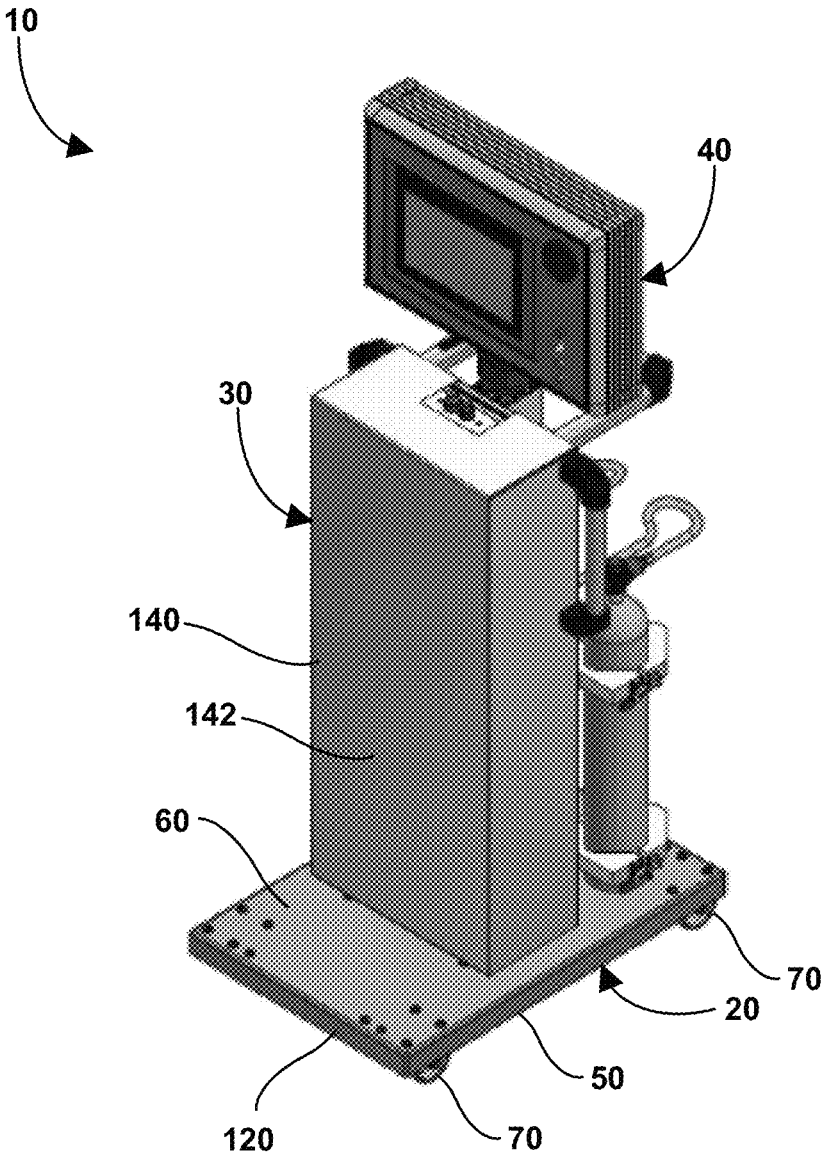
FIG. 1 is a perspective view of a ventilator according to an embodiment.
Figure 2:
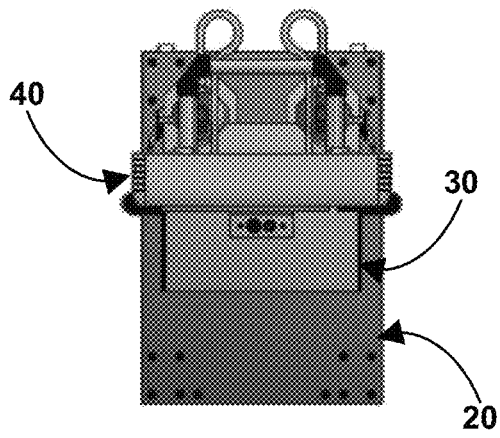
FIG. 2 is a top planar view of the ventilator of FIG. 1.
Figures 6, 7, 8:
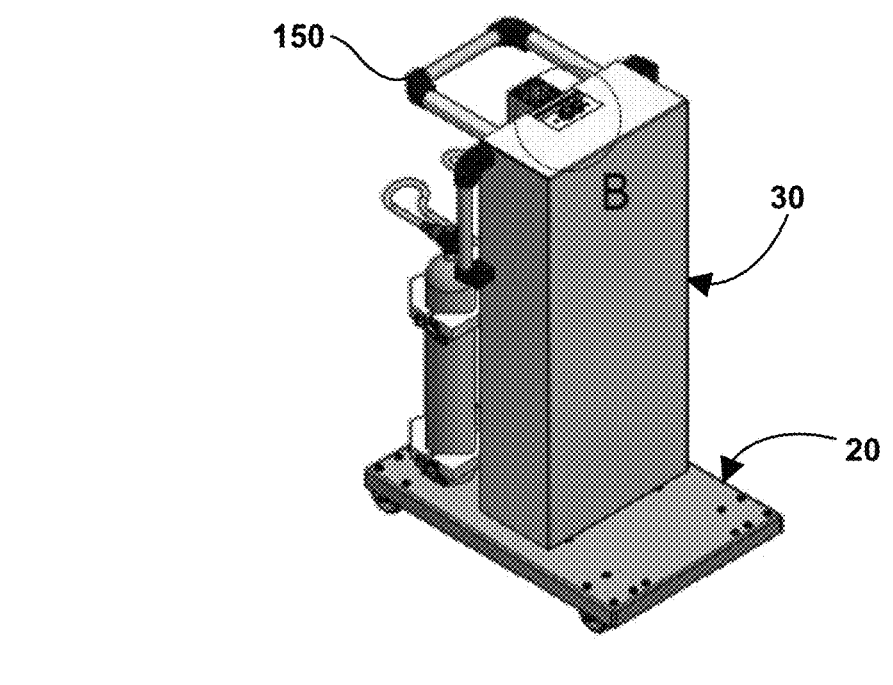
FIG. 6 is a partial perspective view of the ventilator of FIG. 1.
FIG. 7 is a detail view of region B of the ventilator of FIG. 6.
FIG. 8 is a partial perspective view of the ventilator of FIG. 1.

Referring to the figures and first to FIG. 1, there is shown ventilator 10 according to an embodiment. Ventilator 10 includes platform 20, body 30 and input/output device 40. Platform 20 is rectangular in shape and includes base frame 50 upon which support plate 60 is arranged to support body 30 and input/output device 40. Four swivel casters 70 are each connected near respective corners of platform 20 such that ventilator 10 is rollable and moveable. Swivel casters 70 preferably are the type that are anti-static such that an electric charge does not accumulate on ventilator 10 when it is moved. At least one of swivel casters 70, and preferably at least two of them, includes a brake (not shown) that can be manually operated to secure ventilator 10 in a fixed position. Platform 20 may also be adapted to support at least two gas cylinders or bottles, and in the illustrated embodiment air cylinder 80 and oxygen cylinder 90 (best seen in FIG. 8), that are mounted vertically near end 100 and secured to ventilator 10 by brackets 110, which can be v-block type brackets with quick release straps 115. Although cylinders 80 and 90 can be mounted in other configurations, applications are typically restricted to the vertical orientation due to safety regulations on the handling and storing of pressurized cylinders. Platform 20 has a larger footprint than body 30 and input/output device 40 to provide stability to ventilator 10, which reduces the likelihood of the ventilator teetering when it's moved and allows end 120 to be pushed under a patient's bed or surgery table.

Figure 3:
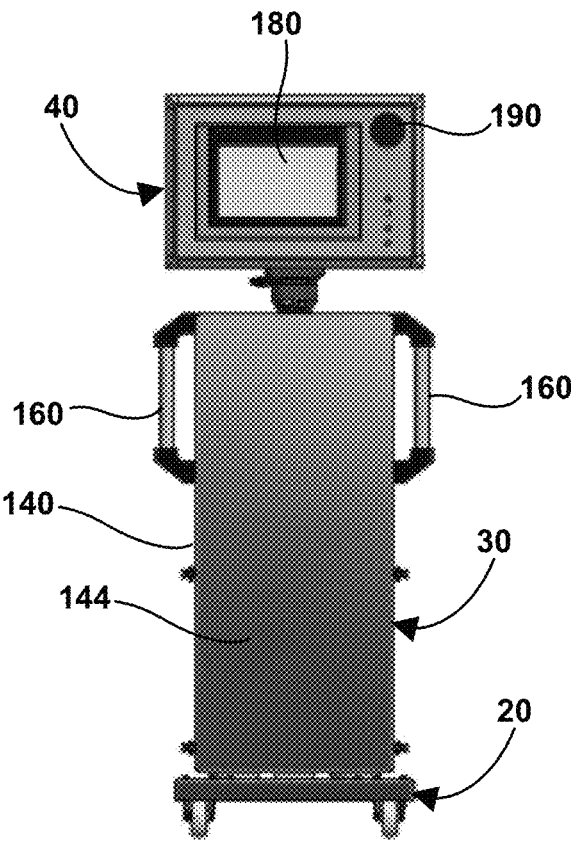
FIG. 3 is an elevational view of the ventilator of FIG. 1.
Figure 4:
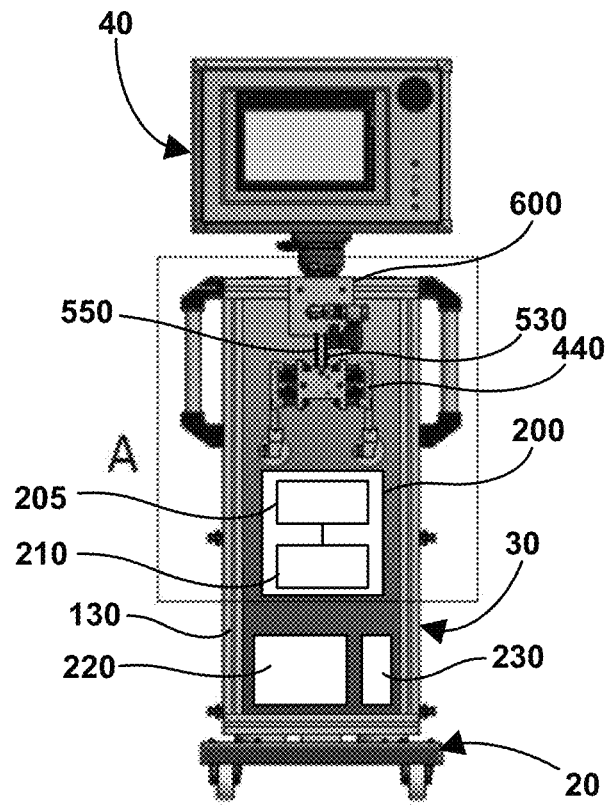
FIG. 4 is an elevational view of the ventilator of FIG. 1 with a panel removed.

Body 30 includes upper frame 130 (best seen in FIG. 4) upon which enclosure 140 is arranged. Enclosure 140 includes box 142 that includes a top, a bottom and three sides and removeable access plate 144 (best seen in FIG. 3) that when combined with box 142 forms a fully enclosed body 30. Preferably enclosure 140 is fabricated from stainless steel. In an exemplary embodiment, box 142 and access plate 144 can be laser cut from plate metal, and box 142 can be folded into the box form illustrated in FIG. 1. In alternative embodiments plate 60 of platform 20 can act as the bottom of enclosure 140 such that box 142 would then have four sides (the top and three sides). Enclosure 140 encloses various components of ventilator 10, such as circuit components and electronics as will be described in more detail below. Rear handle 150 (best seen in FIG. 6) and a pair of side handles 160 (best seen in FIG. 3) provide a means for a healthcare worker to grasp and move ventilator 10 around. As used herein, terms like rear, front, top, bottom, upper and lower are employed to provide a frame of reference when discussing ventilator 10 and are not necessarily to be taken literally, since for example a rear of ventilator 10 in one context such as a patient's context can be considered a front of ventilator 10 in another context such as a healthcare worker's context. Rear handle 150 is suited for pushing the ventilator through a facility, such as a hospital, and side handles 150 can be employed to help position ventilator 10 next to a bed or surgery table.

Base frame 50 (seen in FIG. 1) and upper frame 130 (seen in FIG. 4) are preferably constructed from aluminum extrusion, which is a common form of aluminum that can be assembled quickly and inexpensively. Additionally, aluminum extrusion including closed-off t-slots is easy to clean and is a material known to be used in medical equipment.

Ventilator 10 also includes central post 170 (best seen in FIG. 8) that is securely connected with platform 20, and preferably with frame 50 of the platform, and extends vertically therefrom. Central post 170 provides a rigid support to secure body 30 and input/output device 40 and to attach and secure other equipment associated with ventilator 10, such as brackets 110 employed for securing air and oxygen cylinders 80 and 90 respectively.

Referring again to FIG. 3, input/output device 40 includes touchscreen 180 (and preferably with an integrated operating system) and encoder wheel 190 positioned adjacent the touchscreen. Parameters associated with the use of ventilator 10 (such as tidal volume or inhale pressure as will be described in more detail below) are displayed on touchscreen 180 in one or more views. Each parameter can be adjusted by selecting the parameter by touching a respective portion of touchscreen 180 associated with that parameter and rotating encoder wheel 190 to cause a value of the parameter to change. Indicator lights 195 are positioned adjacent touchscreen 180 below encoder wheel 190 in the illustrated embodiment and provide visible status information related to ventilator 10, such as alarms, warnings and operational readiness, and can be mono-coloured or multi-coloured light emitting diodes (LEDs) or other types of lights. As an example, status information can include air-supply pressure and temperature, oxygen-supply pressure and temperature, flow meter pressure level and temperature, battery power level, fluid injector diagnostics, mixture pressure and temperature, settable peak inlet pressure level, settable $CO_2$ and blood $O_2$ alarms, settable volume flow limits (for PCV control), settable PEEP limits, settable gas temp limits, and cough/distress detection via pressure abnormalities.

Figure 5:
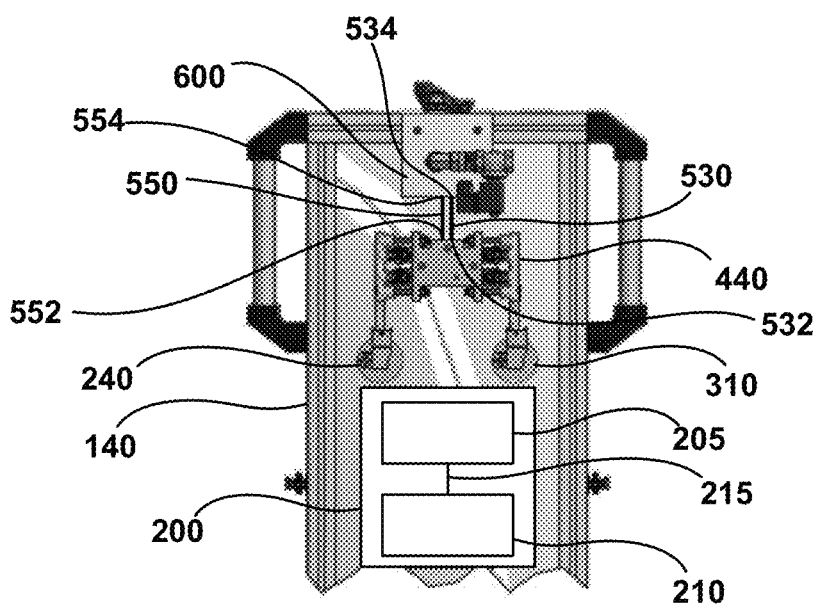
FIG. 5 is a detailed view of region A of the ventilator of FIG. 4.
Figure 12:
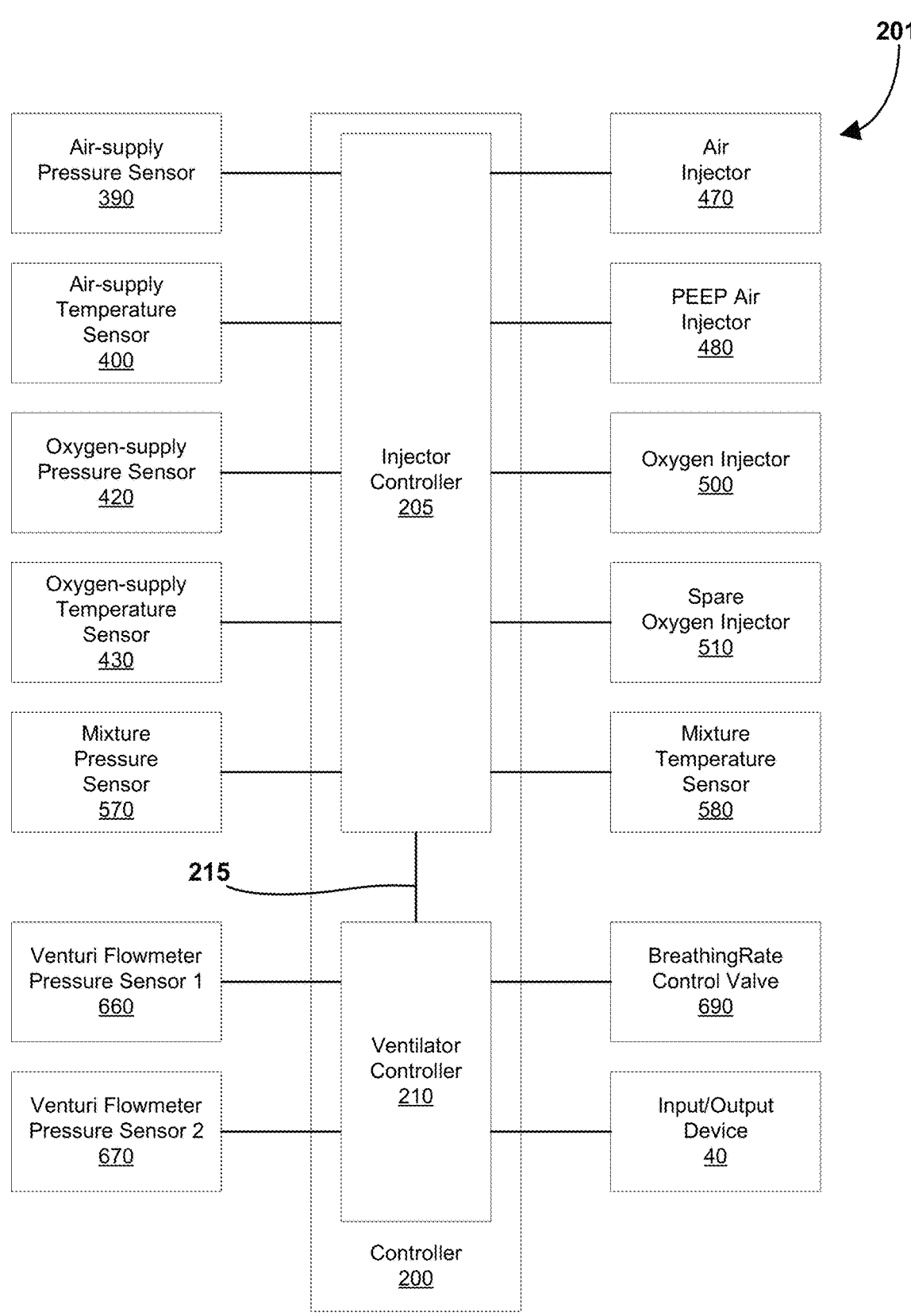
FIG. 12 is a schematic view of a control system of the ventilator of FIG. 1.

Referring to FIGS. 5 and 12, ventilator 10 also includes controller 200 that in the illustrated embodiment includes injector controller 205 and ventilator controller 210. Controllers 205 and 210 are operatively connected with each other over communication link 215, which can be one or more digital communication links and/or one or more analogue communication links. For example, communication link 215 can include a CAN communication bus. Injector controller 205 controls the actuation of fluid injectors that inject air from air cylinder 80 and oxygen from oxygen cylinder 90, which will be described in more detail below, and is responsible for delivering commanded quantities of air and oxygen, and other fluids in other embodiments. Ventilator controller 210 is responsible managing breathing rate control and the delivery of fluids to the patient, and in this regard ventilator controller 210 commands the injector controller 205 to deliver the commanded quantities of air and oxygen, and the other fluids in the other embodiments. Ventilator controller 210 interfaces with input/output device 40 for displaying status information to a healthcare professional and for receiving commands from the healthcare professional for controlling ventilator 10. Controller 200 communicates with and/or commands the various sensors and actuators employed in ventilator 10, as will be described in more detail below, and together controller 200 and the various sensors and actuators is represented as control system 201 in FIG. 12. Controllers 205 and 210 can include both hardware and software components. The hardware components can include digital and/or analog electronic components. In the illustrated embodiment controllers 205 and 210 each include a processor and memories, including one or more permanent memories, such as FLASH, EEPROM and a hard disk, and a temporary memory, such as SRAM and DRAM, for storing and executing a program. As used herein, the terms algorithm, module and step refer to an application specific integrated circuit (ASIC), an electronic circuit, a processor (shared, dedicated, or group) and memory that execute one or more software or firmware programs, a combinational logic circuit, and/or other suitable components that provide the described functionality. In exemplary embodiments the algorithms, modules and steps herein are part of electronic controllers 205 and 210. In other embodiments controllers 205 and 210 can be replaced by a single controller that combines the functionality of controllers 205 and 210.

Ventilator 10 can either be powered by 100 Vac-240 Vac standard mains-electricity supply or by battery 220 that operates at twelve volts dc (12 Vdc). Charging system 230 is included with ventilator 10 such that when the ventilator is plugged in the standard mains-electricity supply (for example, a wall outlet in a hospital) the charging system can charge battery 220. Although only one battery 220 is illustrated, preferably ventilator 10 includes two batteries 220 such that one of the batteries can be changed without stopping the ventilator (referred to as hot swapping). Controller 200 includes a voltage regulator to ensure there is a constant 12 Vdc supply. Battery 220, charging system 230 and other related power supply equipment are preferably located at a bottom of enclosure 140, which helps to lower the center of gravity of ventilator 10.

Figure 11:
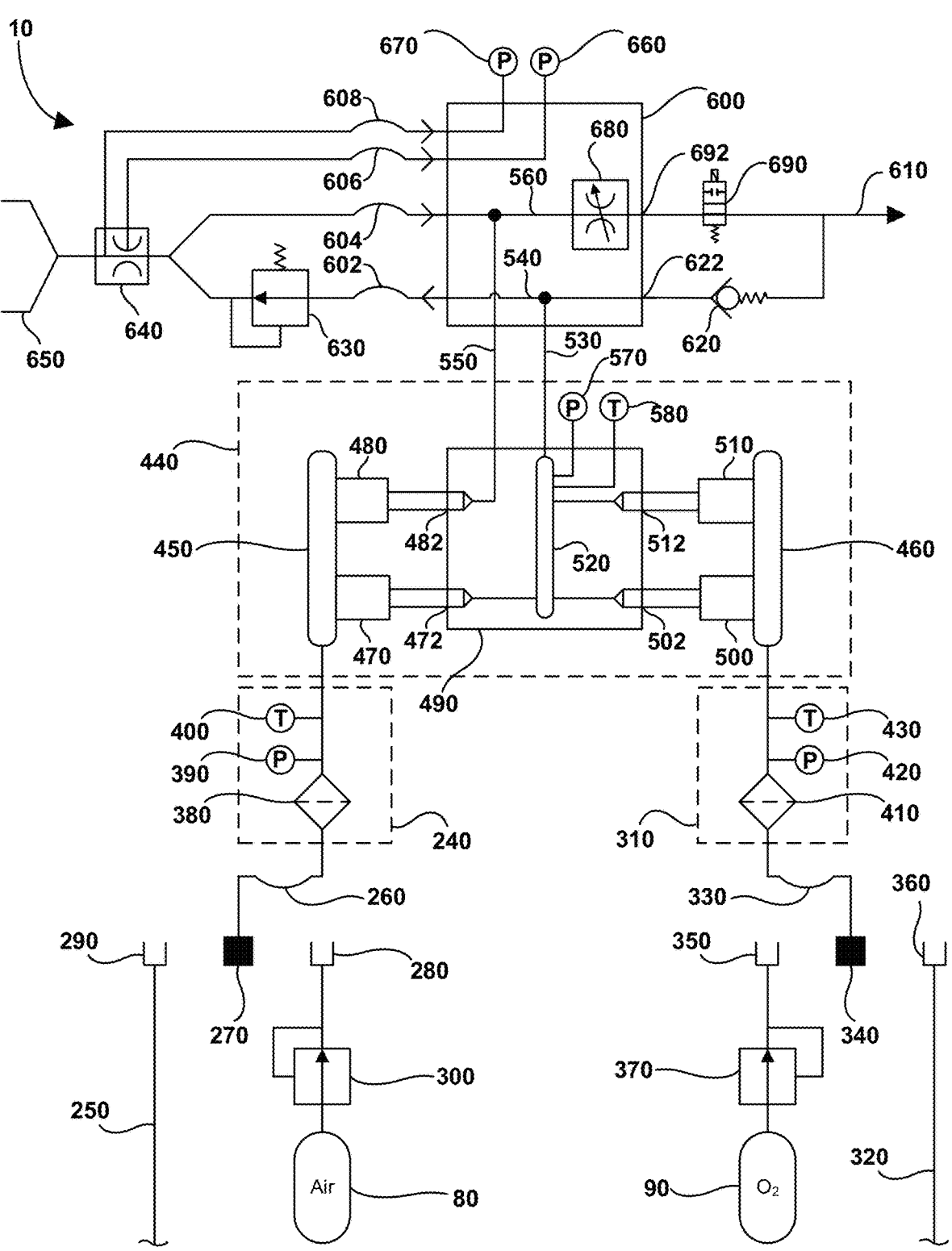
FIG. 11 is a schematic view of the ventilator of FIG. 1.

With reference to FIGS. 5 and 11, air filter assembly 240 is selectively fluidly connected with either air cylinder 80 or with external air supply 250 (seen in FIG. 11) such as a hospital air ring main supply. Air filter assembly 240 connects through hose 260 to male connector 270, which in the illustrated embodiment is a male Schrader valve connection. Female connectors 280 and 290, in the form of female Schrader valve connections in the illustrated embodiment, are associated with air cylinder 80 and external air supply 250 respectively and are selectively connected with male connector 270. The hospital air ring main supply is typically maintained at a desired air supply pressure, for example 4 bar. Regulator 300 regulates air pressure to the desired air supply pressure. For all connectors herein, in other embodiments, the sex between respective mating connectors can be reversed.

Oxygen filter assembly 310 is selectively fluidly connected with oxygen cylinder 90 or with external oxygen source 320 (seen in FIG. 11) such as a hospital oxygen ring main supply. Oxygen filter assembly 310 connects through hose 330 to male connector 340, which in the illustrated embodiment is a male Schrader valve connection. Female connectors 350 and 360, in the form of female Schrader valve connections in the illustrated embodiment, are associated with oxygen cylinder 90 and external oxygen supply 320 respectively and are selectively connected with male connector 340. The hospital oxygen ring main supply is typically maintained at a desired oxygen supply pressure, for example 4 bar. Regulator 370 regulates air pressure to the desired air supply pressure. Air and oxygen regulators 300 and 370 respectively are preferably medical standard pin index regulators that ensure that the correct type of fluid (in this case air and oxygen respectively) are connected to regulators 300 and 370.

Air-filter assembly 240 includes filter 380, pressure sensor 390 and temperature sensor 400. Pressure sensor 390 measures air-supply pressure and temperature sensor 400 measures air-supply temperature downstream from regulator 300 and filter 380. Oxygen-filter assembly 310 includes filter 410, pressure sensor 420, and temperature sensor 430. Pressure sensor 420 measures oxygen-supply pressure and temperature sensor 430 measures oxygen-supply temperature downstream from regulator 370 and filter 410. Although sensors 390 and 400 are included in air-filter assembly 240 and sensors 420 and 430 are included in oxygen-filter assembly 310, in other embodiments these sensors do not need to be part of these assemblies and can be installed into ventilator 10 individually and separately.

Figure 9:
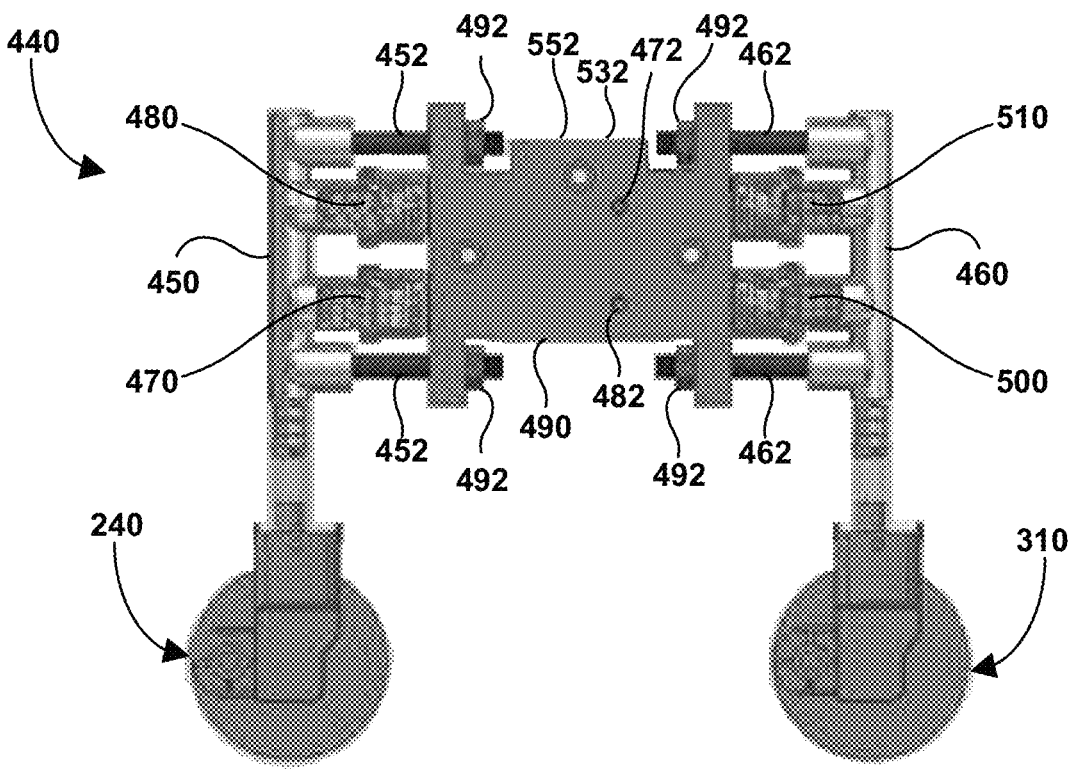
FIG. 9 is a partial elevational view of the ventilator of FIG. 5.

Referring to FIGS. 5, 9 and 11, injector manifold assembly 440 includes air rail 450 fluidly connected with air-filter assembly 240 to receive filtered air, and oxygen rail 460 fluidly connected with oxygen-filter assembly 310 to receive filtered oxygen. Rails 450 and 460 allow storage of a predetermined volume of air and oxygen respectively, and can be an accumulator, a conduit, a pipe or other type of fluid container. Rails 450 and 460 can be connected to their respective filter assemblies 240 and 310 through rigid and/or flexible conduits. Air injectors 470 and 480 are connected with air rail 450 and with injector manifold 490, and oxygen injectors 500 and 510 are connected with oxygen rail 460 and with injector manifold 490. In the illustrated embodiment air injectors 470 and 480 are connected directly to air rail 450 and to ports 472 and 482 in injector manifold 490, and oxygen injectors 500 and 510 are connected directly to oxygen rail 460 and to ports 502 and 512 in injector manifold 490; however, this is not a requirement and in other embodiments each injector 470, 480, 500 and 510 can be connected to their respective rail 450, 460 and/or respective ports 472, 482, 502 and 512 in injector manifold 490 through rigid and/or flexible conduits. Injector manifold 490 significantly reduces the amount of pipe work and fittings required, which simplifies the layout in enclosure 140 (seen in FIG. 5) and reduces the assembly time of ventilator 10. Injector manifold 490 has a plurality of through holes with a space for nuts 492 (seen in FIG. 9) to be fitted to studs 452 in air rail 450 and studs 462 in oxygen rail 460 whereby tightening nuts 492 will pull air rail 450 and oxygen rail 460 onto respective injectors 470, 480, 500 and 510 and sandwich the injectors between the rails and the injector manifold. In an exemplary embodiment injector manifold 490 is made from a thermoplastic, such as Delrin, or other similarly suitable material for absorbing sound generated by injectors 470, 480, 500 and 510. Injectors 470, 480, 500 and 510 are positioned opposite each other, and more particularly air injector 470 is positioned opposite oxygen injector 500 and air injector 480 is positioned opposite injector 510, whereby controller 200 can actuate respective pairs of injectors at the same time in a manner to have a noise cancelling effect.

In an exemplary embodiment fluid injectors 470, 480, 500 and 510 are automotive-type-gaseous-fuel injectors that include an injection valve and a solenoid that is actuated to open the injection valve during an injection event to deliver precise quantities of fluid per injection, also known as commanded quantities. In other embodiments different types of fluid injectors can be employed, including fluid injectors that are hydraulically actuated. The quantity of fluid injected is controlled by the opening time and opened time of each of the injectors, which is collectively referred to herein as the opened time. The opened time of each fluid injector 470, 480, 500 and 510 is controlled by controller 200 that generates respective electrical signals that have respective pulse widths that actuate respective fuel injectors. The actuation of each of the injectors is compensated against changes in injection pressure in order to deliver a desired quantity of fluid. Injection pressure is defined herein as a difference between upstream fluid pressure and downstream fluid pressure with respect to a closed injection valve (it is understood that injection pressure changes during injection events due to changes in pressure upstream and downstream of the opened injection valve). Changes in pressure and temperature of a fluid upstream and of a fluid downstream of an injection valve can alter an injection pressure for the injection valve. In an exemplary embodiment, injectors 470, 480, 500 and 510 can deliver between 2 milliliters (ml) and 100 ml of fluid (that is, air or oxygen) per injection when the injection pressure is around 4 bar, and can be actuated between one (1) shot per second and forty (40) shots per second. A typical healthy human breath requires approximately 500 ml of air per breath cycle (also known as the 'tidal volume'), and the breath rate is typically 10-12 breaths per minute, for a total gas exchange volume rate of approximately 5-6 litres/minute.

Air injector 470 is configured to introduce (that is, inject) air from air rail 450 into mixing chamber 520 within manifold 490. Oxygen injector 500 and 510 are both configured to introduce (that is, inject) oxygen from oxygen rail 460 into mixing chamber 520. Oxygen injector 510 may be employed as a backup injector for oxygen injector 500 and is not required in other embodiments. An air and oxygen mixture can be formed within mixing chamber 520 by selective activation of air injector 470 and oxygen injectors 500 and 510. Since air contains 20.95% oxygen by volume already, the mixture formed in mixing chamber 520 can be considered an oxygen-enhanced air mixture, and the percentage of oxygen in the oxygen-enhanced air mixture can theoretically vary between 20.95% oxygen content by volume (no enhancement) up to 100% oxygen content by volume (no air). The gas injection approach is hugely dynamic in capability. For example, it has the capability to deliver 100% air in one breath and 100% oxygen in the next. Alternatively, a high concentration of oxygen can be delivered at the start of the breath and a low concentration later on in the breath to target oxygen delivery further down into the lungs. Still further, a desired oxygen concentration can be targeted for delivery to one or more different regions of the respiratory system by adjustably varying the oxygen concentration during selected timeframes during the inhalation cycle.

In other embodiments a dosing injector can be added to injector manifold assembly 440, or alternatively, rather than injector 510 a dosing injector may be employed. A dosing injector is employed to inject a drug or other substance, which can be in a liquid state and/or a gaseous state, into mixing chamber 520 for delivery to the lungs by phasing injection such that it targets different areas of the lung according to time of injection during the breath. Mixing chamber 520 is fluidly connected to inhalation pathway 540 by conduit 530. Mixing chamber 520 and/or conduit 530 (acting as a restriction orifice) can operate as a dampener, or low pass filter, to remove pressure pulsations caused by injection of the fuel injectors. A restriction orifice can be located at alternative locations along inhalation pathway 540 in order to remove pressure pulsations caused by injection of fluids. Injector manifold 490 include a port for fluid connection with conduit 530. In other embodiments injector manifold 490 can includes a port fluidly connected to mixing chamber 520 and to a green hospital bag that allows a healthcare professional to manually fill a patient's lungs.

Air injector 480 is configured to introduce air into manifold 490 for delivery to exhalation pathway 560 by conduit 550. Injector manifold 490 includes a port for fluid connection with conduit 550. Air injector 480 is employed to generate positive end-expiratory pressure (PEEP). PEEP is a mode of therapy used in conjunction with mechanical ventilation. At the end of mechanical or spontaneous exhalation, PEEP maintains a patient's airway pressure above atmospheric pressure by exerting pressure that opposes passive emptying of the lung. This pressure is typically achieved by maintaining a positive pressure flow at the end of exhalation, also referred to as a back pressure. PEEP therapy can be effective when used in patients with a diffuse lung disease that results in an acute decrease in functional residual capacity (FRC), which is the volume of gas that remains in the lung at the end of a normal expiration. FRC is determined by primarily the elastic characteristics of the lung and chest wall.

Pressure sensor 570 and temperature sensor 580 measure mixture pressure and mixture temperature respectively of the mixture in mixing chamber 520. Injector manifold 490 includes ports 472 and 482 (seen in FIG. 9) for fluid connection with sensors 570 and 580 respectively. Air-supply pressure and mixture pressure can be employed to determine air-injection pressure. Oxygen-supply pressure and mixture pressure can be employed to determine oxygen-injection pressure. Mixture density can be determined by mixture pressure, mixture temperature and a mass mixture ratio between injected air and injected oxygen in mixture chamber 520. The mass mixture ratio can be determined based on a mass of air injected into mixing chamber 520 relative to a mass of oxygen injected into the mixing chamber. Air-supply pressure and temperature can be employed to determine air-supply density, and oxygen-supply pressure and temperature can be employed to determine oxygen-supply density. The mass of air injected per injection event can be determined based on the air-supply density, the air-injection pressure and the on-time of air injector 470 or 480. The mass of oxygen injected per injection event can be determined based on the oxygen-supply density, the oxygen-injection pressure and the on-time of oxygen injector 500 or 510.

Figure 10:
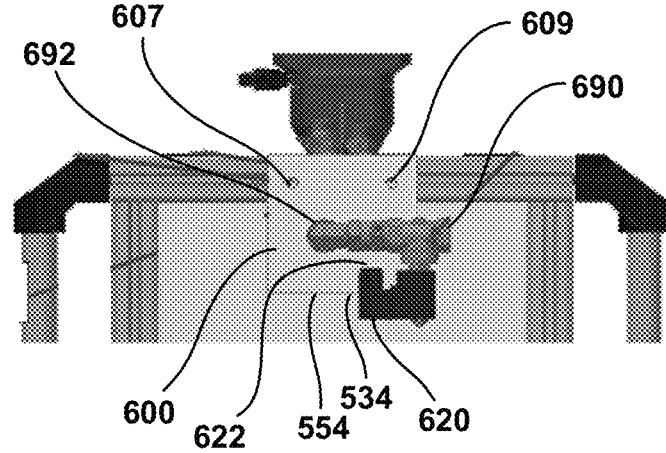
FIG. 10 is a partial elevational view of the ventilator of FIG. 6.

Piping manifold 600 is positioned at the top of enclosure 140 and preferably has two fluid connections with injector manifold 490 and four fluid connections to the patient. Mixture conduit 530 (seen in FIGS. 5 and 11) for inhale extends between port 532 (seen in FIG. 9) in injector manifold 490 and port 534 (seen in FIG. 10) in piping manifold 600. PEEP conduit (seen in FIGS. 5 and 11) for exhale extends between port 552 (seen in FIG. 9) in injector manifold 490 and port 554 (seen in FIG. 10) in piping manifold 600. The four fluid connections to the patient are by way of flexible hose connections 602, 604, 606, and 608, seen in FIG. 11. Hose 602 fluidly connects to inhalation pathway 540 at port 542 (seen in FIG. 7). Hose 604 fluidly connects to exhalation pathway 560 at port 562 (seen in FIG. 7). Hoses 606 and 608 are capillary tube connections between venturi flow meter 640 and ports 607 and 609 (seen in FIG. 10) in piping manifold 600. A majority of piping manifold 600 is within enclosure 140 except for a portion that protrudes out of a top of the enclosure (best seen in FIGS. 5 and 7) where hoses 602, 604, 606 and 608 to the patient are connected. Piping manifold 600 is configured to be along inhalation pathway 540 between the patient and mixing chamber 520, and along exhalation pathway 560 between the patient and drain conduit 610 connected, for example, to a hospital extraction system. Pressure relief valve 620 is connected to port 620 (seen in FIG. 9) in piping manifold 600 and fluidly connected to inhalation pathway 540 and acts as a safety device to ensure inhalation pressure does not rise above a maximum inhalation pressure. In an exemplary embodiment the maximum inhalation pressure is set to 70 centimeters of water ($cmH_2O$). An output of pressure relief valve 620 is fluidly connected to drain conduit 610 for extraction. Adjustable pressure limit (APL) valve 630 is connected with piping manifold 600 through flexible hose 602 and with venturi flowmeter 640. APL valve 630 allows excess fresh mixture flow and exhaled gases from the patient to leave the system while preventing additional mixture from mixing chamber 520 from entering (that is, it prevents back flow during the exhalation cycle). Venturi flowmeter 640 is fluidly connected with patient mouthpiece 650. Venturi flowmeter pressure sensors 660 and 670 are connected to ports 662 and 672 (seen in FIG. 7) respectively in piping manifold 600 and are fluidly connected to hoses 606 and 608 respectively. Venturi flowmeter pressure sensors 660 and 670 can be employed in place of pressure sensor 570 that measures mixture pressure in mixing chamber 520. Similarly, temperature sensor 580 that measures mixture temperature in mixing chamber 520 although does improve the operation of ventilator 10 it is not required in other embodiments. Exhalation pathway 560 passes through variable-flow restriction valve 680 in piping manifold 600. Variable-flow restriction valve 680 is adjusted along with PEEP air injector 480 to control back pressure. In other embodiments variable-flow restriction valve 680 can be replaced with a fixed restriction orifice. Breathing rate of the patient is controlled by the opening and closing of breathing-rate-control valve 690, which preferably is an electrically operated diaphragm valve, but can be other types of valves in other embodiments. Breathing-rate-control valve 690 is fluidly connected to port 692 (seen in FIG. 10) and to exhalation pathway 560.

Figure 13:
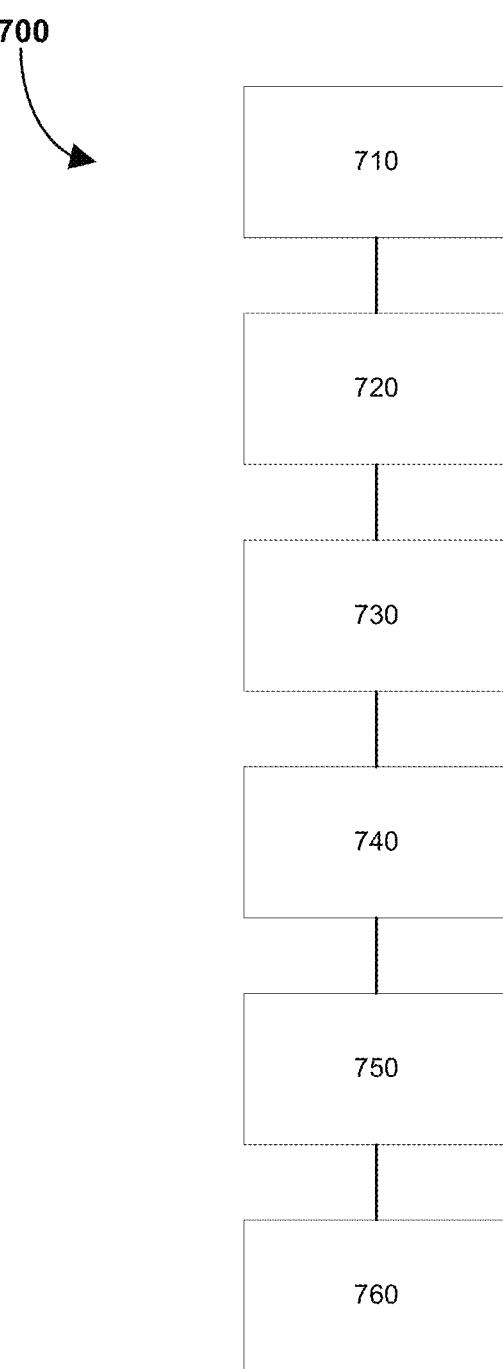
FIG. 13 is a flow chart view of an algorithm for setting up the ventilator of FIG. 1 to operate in the PCV mode of operation.

Preferably, controller 200 can selectively perform self-diagnostic checks including pressure decay test for leaks, pressure and temperature sensor calibration, flow meter calibration and fluid injector calibration. With reference to FIG. 13, algorithm 700 in controller 200 for setting up ventilator 10 for the PCV mode of operation includes, for example, setting inhale pressure (Pinsp) in step 710 at a level between a range (e.g. 0-60 $cmH_2O$), setting breathing rate (respiration rate RR) in step 720 at a level within a range (e.g. 0-30 p/min), setting I:E ratio (inhale to exhale time ratio) in step 730 at a level within a range (e.g. 5:1 to 1:5), setting PEEP (back pressure) in step 740 at a level within a range (e.g. 0-12 $cmH_2O$), setting maximum inhalation pressure (PMax) in step 750 at a level within a range (e.g. 0-100 $cmH_2O$), setting pressure rise rate in step 760 at a level within a range (e.g. 1-10 fastest to slowest). The steps in algorithm 700 can be performed in a different order than illustrated and described. In other embodiments ventilator 10 can be setup in the VCV mode of operation by a calculation methodology.

Figure 14:
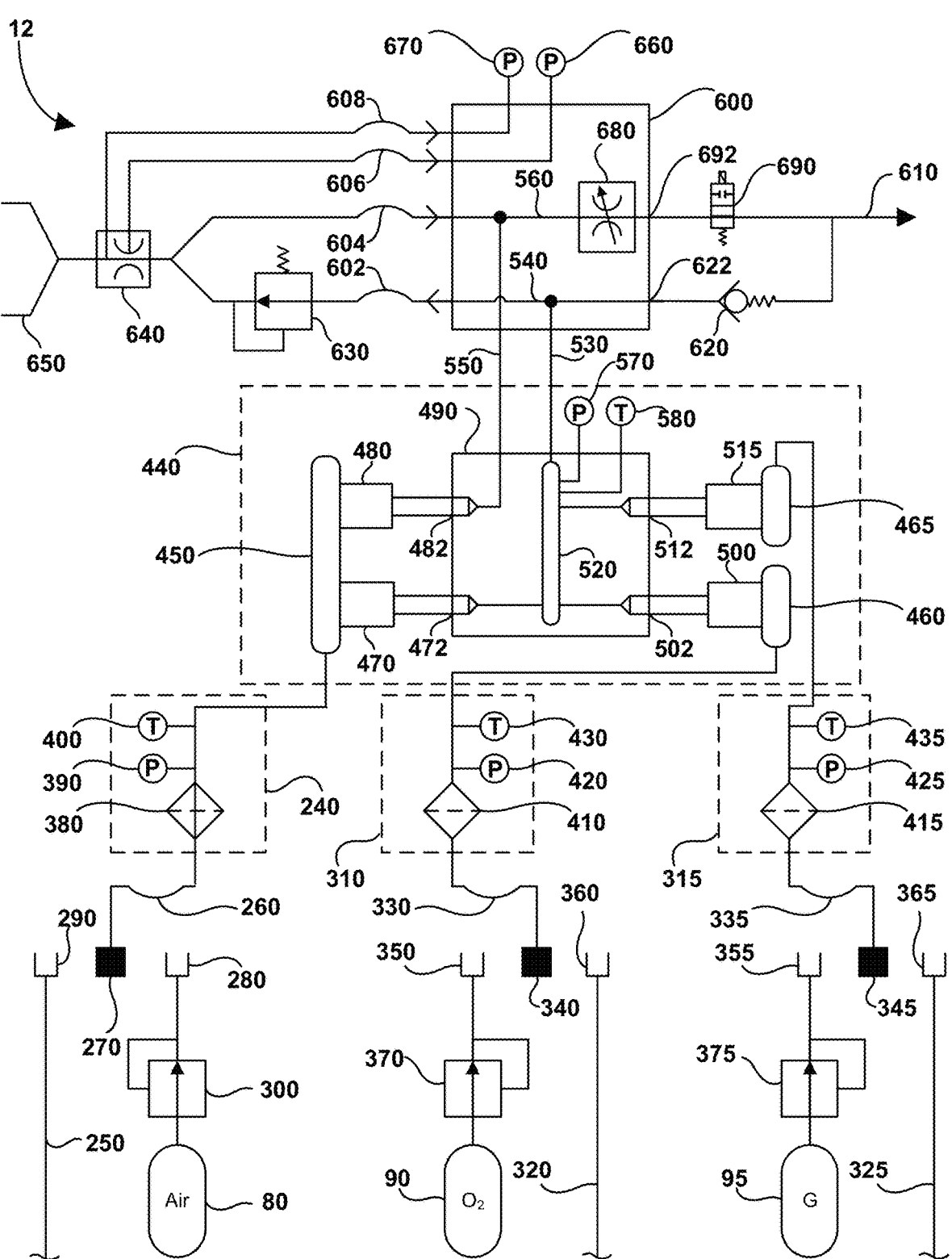
FIG. 14 is a schematic view of a ventilator according to another embodiment.

Referring now to FIG. 14, there is shown ventilator 12 according to another embodiment of the present disclosure. Elements in common with other embodiments illustrated herein are referenced by the same reference numbers, and if they operate and function in the same way, may not be described again in relation to other embodiments. In addition to air injectors 470, 480 and oxygen injector 500, ventilator 12 includes a fourth fluid injector 515 configured to selectively introduce (that is, inject) a fluid from a separate fluid supply such as vessel 95 (arranged on ventilator 12) and/or external separate fluid supply 325. Vessel 95 may be a cylinder of compressed gaseous fluid or another supply source capable of delivering fluid at a desired supply pressure to rail 465 and/or in some embodiments directly to fourth injector 515. Fourth fluid injector 515 may be configured to introduce (separately and independently from that of injectors 470, 480 and 500) a quantity of fluid into mixing chamber 520 by controlling the opening time and opened time of injector 515 where the actuation of the injector is similarly compensated against changes in injection pressure in order to deliver a desired quantity of fluid. Optional filter assembly 315 connects through hose 335 to male connector 345, which in the illustrated embodiment can be a male Schrader valve connection. Female connectors 355 and 365, in the form of female Schrader valve connections in the illustrated embodiment, are associated with supply 95 and 325 respectively and are selectively connected with male connector 345. Regulator 375 regulates fluid pressure to the desired fluid supply pressure, but it is understood that depending on the type of fluid to be introduced to mixing chamber 520, regulator 375 may not be required. Similar to air and oxygen regulators 300 and 370, regulator 375 is preferably medical standard pin index regulators that ensure that the correct type of fluid is connected to regulator 375. Filter assembly 315 includes filter 415, pressure sensor 425, and temperature sensor 435. Pressure sensor 425 measures fluid-supply pressure and temperature sensor 435 measures fluid supply temperature downstream from regulator 375 and filter 415. Although sensors 425 and 435 are included in fluid filter assembly 315, in other embodiments these sensors do not need to be part of these assemblies and can be installed into ventilator 12 individually and separately. Pressure and temperature sensors 425 and 435 send their respective measurement signals to controller 200, which is adapted to the current embodiment, and controller 200 controls the actuation of third fluid injector 515.

Figure 15:
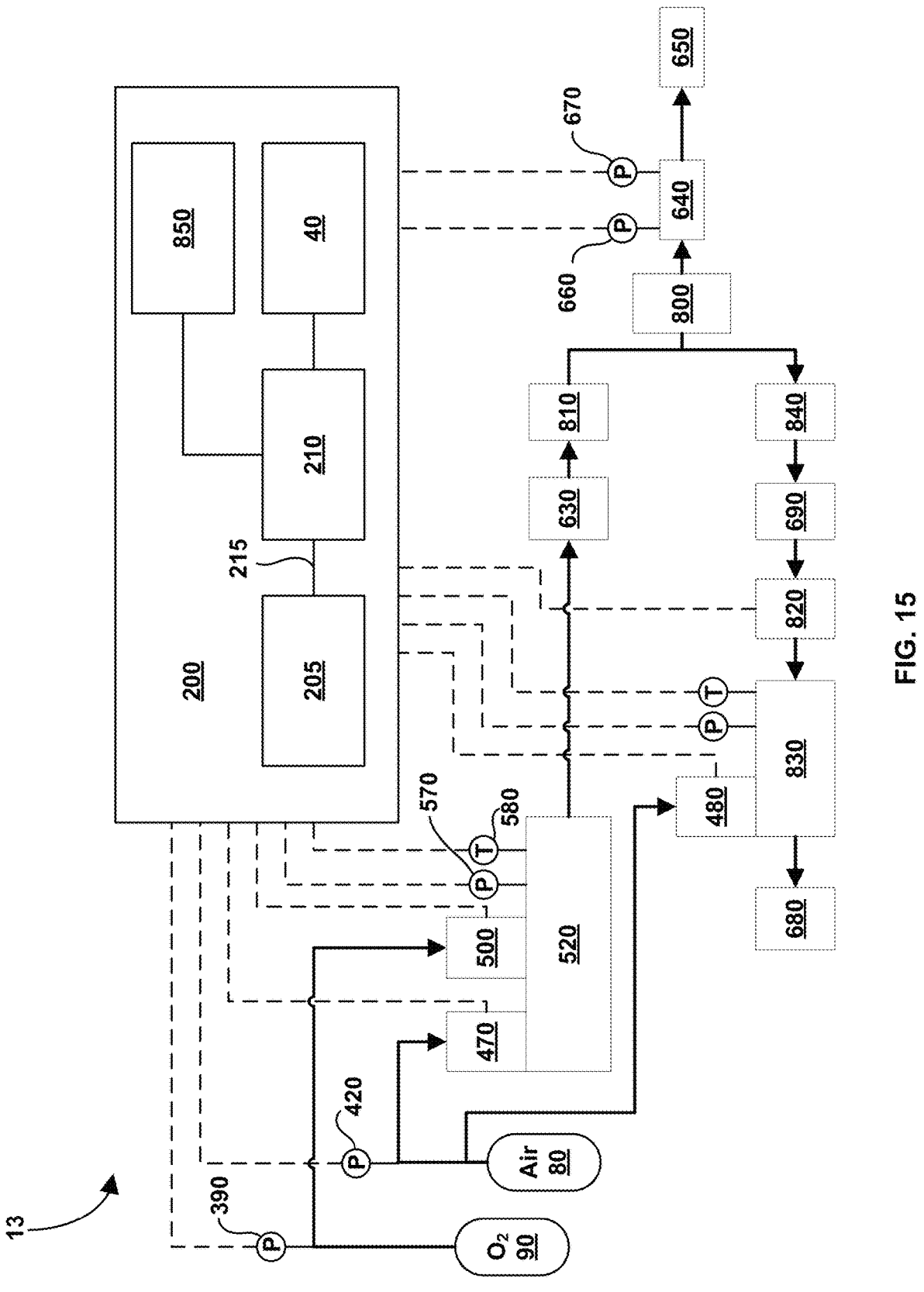
FIG. 15 is schematic view of a ventilator according to another embodiment.

Referring now to FIG. 15, there is shown ventilator 13 according to another embodiment where like reference numerals to the previous embodiment have like reference numerals and may not be discussed in detail if at all. In this embodiment solid lines between elements represents fluid connections, such as air and oxygen, and dashed lines between elements represents control system connections, such as electromagnetic signals. Filter 800 is a mouthpiece filter for filtering fluids to (mostly) and from the patient. Filter 810 is located at an end of an inhalation pipe before it merges with an exhalation pipe, and filter 820 is located at an end of the exhalation pipe. Chamber 830 accepts injections from PEEP air injector 480, which is employed in cooperation with variable-flow restriction valve 680 (or a fixed restriction orifice in other embodiments) to generate a back pressure near the end of the exhalation cycle. Chamber 830 may be an accumulator, a conduit, a pipe or other type of fluid container. Safety valve 840 located along the exhalation pathway allows a patient to breathe through safety valve 840 in the event there is a failure somewhere along the inhalation pathway. Safety valve 840 can be opened by the patient or healthcare professional by manually depressing an actuator (not shown) on safety valve 840. Networking controller 850 allows communications with other ventilators for multi-ventilator monitoring. All embodiments herein can include networking controller 850 and can communicate with a network and/or networked ventilators in other embodiments.

Ventilators 10, 12 and 13 by employing fluid injectors 470, 480, 500 and 510/515 is remarkably a very accurate and dynamic technique for delivering the correct mixture ratio and quantity of oxygen and air to a patient. Ventilator embodiments herein are pressure control ventilators. The injector control software employed in controller 205 is similar to gaseous-fuel injector control software already employed in low-pressure gaseous-fuel automotive applications, which has been proven effective in extremely demanding operating conditions, since both applications operate with comparable fluid pressures. This control software also compensates for lower air and oxygen supply pressures (for example, as air cylinder 80 and oxygen cylinder 90 start to run out). Several of the components are borrowed from the automotive industry (such as fluid injectors 470, 480, 500 and 510/515, rails 450, 460 and 465, filter assemblies 240, 310 and 315, and controller 205) and are relatively low cost since they are mass produced for automotive applications and are off the shelf and available in large quantities. Ventilators disclosed herein are designed to operate from a 12 Vdc voltage. For hospital use, a mains to 12V converter is employed, but fundamentally the ventilator can operate from a 12V battery in the field, in the ambulance, in the hospital corridor, and in less developed countries. A standard car battery can provide several hours of operation, for example approximately eight (8) hours. Ventilators 10, 12 and 13 are transportable while continuing to offer full mechanical ventilation and monitoring as the patient is trolleyed to and from ambulance to an intensive care unit or hospital room.

In other embodiments ventilators 10, 12 and 13 can include a vacuum facility selectively fluidly connected to exhalation pathway 560. The vacuum facility when fluidly connected to exhalation pathway 560 can extract fluids from the lungs. The vacuum facility can be a connection to an external vacuum system in a hospital or can include a vacuum pump in the ventilator to pump fluid out of the lungs.

An improved ventilator for mechanical ventilation during a breathing cycle including an inhalation cycle and an exhalation cycle is disclosed herein, the ventilator is configurable to be in fluid communication with a supply of a first fluid and including an inhalation pathway and an exhalation pathway, the ventilator comprising a first fluid injector in fluid communication with the supply of the first fluid for injecting the first fluid, wherein the inhalation pathway receives the first fluid injected by the first fluid injector; and a controller operatively connected with the first fluid injector and programmed to 1) selectively actuate the first fluid injector to inject the first fluid wherein the first fluid is received in the inhalation pathway such that an inhalation pressure in the inhalation pathway is within a predetermined range during the inhalation cycle. The first fluid can be air.

The ventilator may also be configurable to be in fluid communication with a supply of a second fluid, the ventilator further comprising a mixing chamber in fluid communication with the first fluid injector and with the inhalation pathway, wherein the first fluid injected by the first fluid injector is communicated to the inhalation pathway through the mixing chamber; and a second fluid injector in fluid communication with the supply of the second fluid for injecting the second fluid, wherein the second fluid injected by the second fluid injector is communicated to the inhalation pathway through the mixing chamber; wherein the controller is further programmed to selectively actuate the first fluid injector and the second fluid injector to inject the first fluid and the second fluid respectively to form a mixture of the first fluid and the second fluid in the mixing chamber for inhalation by a patient during the inhalation cycle, wherein a mixture ratio between the first fluid to the second fluid can vary between 0:100 and 100:0; and wherein a mixture pressure of the mixture of the first fluid and the second fluid is within the predetermined range during the inhalation cycle. The second fluid can be oxygen.

The ventilator can further comprise a third fluid injector in fluid communication with the supply of the first fluid for injecting the first fluid, wherein the exhalation pathway receives the first fluid injected by the third fluid injector; and a restriction orifice in the exhalation pathway; wherein the controller is further programmed to selectively actuate the third fluid injector to inject the first fluid wherein the first fluid is received in the exhalation pathway such that an exhalation pressure in the exhalation pathway is within a predetermined range during at least a portion of the exhalation cycle.

The improved ventilator can optionally include a dosing injector fluidly connected to the mixing chamber.

The ventilator may also include a third fluid rail for storage of a predetermined volume of a fluid; the third fluid rail being fluidly connected to a fourth fluid injector for introducing fluid into the mixing chamber. The ventilator controller may be further programmed to selectively actuate any combination of the first fluid injector, the second fluid injector, and the fourth fluid injector to form a mixture of fluids injected respectively therefrom in the mixing chamber for inhalation by a patient during the inhalation cycle, wherein the mixture comprises any combination from 0 to 100 percent of each of the fluids injected respectively therefrom; and wherein a mixture pressure of the mixture of the first fluid, second fluid and fourth fluid is within the predetermined range during the inhalation cycle. The fourth fluid can be oxygen, nitrous oxide or other fluid.

While particular elements, embodiments and applications of the present invention have been shown and described, it will be understood, that the invention is not limited thereto since modifications can be made by those skilled in the art without departing from the scope of the present disclosure, particularly in light of the foregoing teachings.

What is claimed is:

1. A ventilator for mechanical ventilation during a breathing cycle including an inhalation cycle and an exhalation cycle, the ventilator configurable to be in fluid communication with a supply of a first fluid and including an inhalation pathway and an exhalation pathway, the ventilator comprising:

a first fluid injector in fluid communication with the supply of the first fluid for injecting the first fluid, wherein the inhalation pathway receives the first fluid injected by the first fluid injector; and a controller operatively connected with the first fluid injector and programmed to:

selectively actuate the first fluid injector to inject the first fluid wherein the first fluid is received in the inhalation pathway such that an inhalation pressure in the inhalation pathway is within a predetermined range during the inhalation cycle; and wherein the first fluid is air.

2. A ventilator for mechanical ventilation during a breathing cycle including an inhalation cycle and an exhalation cycle, the ventilator configurable to be in fluid communication with a supply of a first fluid and including an inhalation pathway and an exhalation pathway, the ventilator comprising:

a first fluid injector in fluid communication with the supply of the first fluid for injecting the first fluid, wherein the inhalation pathway receives the first fluid injected by the first fluid injector; and a controller operatively connected with the first fluid injector and programmed to:

selectively actuate the first fluid injector to inject the first fluid wherein the first fluid is received in the inhalation pathway such that an inhalation pressure in the inhalation pathway is within a predetermined range during the inhalation cycle, wherein the ventilator is configurable to be in fluid communication with a supply of a second fluid, the ventilator further comprising:

a mixing chamber in fluid communication with the first fluid injector and with the inhalation pathway, wherein the first fluid injected by the first fluid injector is communicated to the inhalation pathway through the mixing chamber; and a second fluid injector in fluid communication with the supply of the second fluid for injecting the second fluid, wherein the second fluid injected by the second fluid injector is communicated to the inhalation pathway through the mixing chamber;

wherein the controller is further programmed to:

selectively actuate the first fluid injector and the second fluid injector to inject the first fluid and the second fluid respectively to form a mixture of the first fluid and the second fluid in the mixing chamber for inhalation by a patient during the inhalation cycle, wherein a mixture ratio between the first fluid to the second fluid can vary between 0:100 and 100:0;

wherein a mixture pressure of the mixture of the first fluid and the second fluid is within the predetermined range during the inhalation cycle.

3. The ventilator of claim 2, wherein the second fluid is oxygen.

4. The ventilator of claim 2, further comprising:

a third fluid injector in fluid communication with the supply of the first fluid for injecting the first fluid, wherein the exhalation pathway receives the first fluid injected by the third fluid injector; and a restriction orifice in the exhalation pathway;

wherein the controller is further programmed to:

selectively actuate the third fluid injector to inject the first fluid wherein the first fluid is received in the exhalation pathway such that an exhalation pressure in the exhalation pathway is within a predetermined range during at least a portion of the exhalation cycle.

5. The ventilator of claim 4, wherein the first fluid is air and the second fluid is oxygen.

6. The ventilator of claim 4, further comprising a dosing injector fluidly connected to the mixing chamber.

7. The ventilator of claim 6, further comprising a third fluid rail for storage of a predetermined volume of a third fluid; the third fluid rail being fluidly connected to a fourth fluid injector for introducing the third fluid into the mixing chamber.

8. The ventilator of claim 7, wherein the controller is further programmed to:

selectively actuate anyone one or more of the first fluid injector, the second fluid injector, and the fourth fluid injector to form a mixture of fluids injected respectively therefrom in the mixing chamber for inhalation by a patient during the inhalation cycle, wherein the mixture comprises any combination from 0 to 100 percent of each of said fluids injected respectively therefrom;

wherein a mixture pressure of the mixture of the first fluid, the second fluid and the third fluid is within the predetermined range during the inhalation cycle.

9. The ventilator of claim 8, wherein the first fluid is air and the second fluid is oxygen.

10. A ventilator comprising:

a first fluid rail for storage of a predetermined volume of a first fluid;

a first fluid injector fluidly connected with the first fluid rail;

a second fluid rail for storage of a predetermined volume of a second fluid;

a second fluid injector fluidly connected with the second fluid rail;

a mixing chamber fluidly connected with the first fluid injector and the second fluid injector and with an inhalation pathway;

a third fluid injector fluidly connected with the first fluid rail and with an exhalation pathway;

a mouthpiece for a patient fluidly connected to the exhalation pathway;

an APL valve fluidly connected to the inhalation pathway and the mouthpiece;

a breathing-rate-control valve fluidly connected to the exhalation pathway and a drain conduit;

a controller operatively connected to the first fluid injector; the second fluid injector, the third fluid injector and the breathing-rate-control valve and programmed to:

actuate the breathing-rate-control valve to generate a breathing cycle including an inhalation cycle and an exhalation cycle;

selectively actuate the first fluid injector and the second fluid injector to inject the first fluid and the second fluid respectively to form a mixture of the first fluid and the second fluid in the mixing chamber for inhalation by a patient during the inhalation cycle, wherein a mixture ratio between the first fluid to the second fluid can vary between 0:100 and 100:0; and actuate the third fluid injector to generate back pressure in the exhalation pathway during an exhalation cycle.

11. The ventilator as claimed in claim 10, wherein the first fluid is air and the second fluid is oxygen.

* * * * *